(12) United States Patent
Hoshino et al.

(10) Patent No.: US 7,465,563 B2
(45) Date of Patent: Dec. 16, 2008

(54) ENZYMATIC PROCESS FOR THE MANUFACTURE OF L-ASCORBIC ACID AND D-ERYTHORBIC ACID

(75) Inventors: Tatsuo Hoshino, Kanagawa-ken (JP); Tatsuya Kiyasu, Kanagawa-ken (JP); Masako Shinjoh, Basel (CH)

(73) Assignee: DSM IP Assets B.V., TE Heerlen (NL)

( * ) Notice: Subject to any disclaimer, the term of this patent is extended or adjusted under 35 U.S.C. 154(b) by 397 days.

(21) Appl. No.: 10/494,886

(22) PCT Filed: Oct. 31, 2002

(86) PCT No.: PCT/EP02/12157

§ 371 (c)(1), (2), (4) Date: May 7, 2004

(87) PCT Pub. No.: WO03/040381

PCT Pub. Date: May 15, 2003

(65) Prior Publication Data

US 2005/0019878 A1    Jan. 27, 2005

(30) Foreign Application Priority Data

Nov. 9, 2001 (EP) .................................. 01126768

(51) Int. Cl.
*C12P 17/04* (2006.01)
*C07D 305/12* (2006.01)

(52) U.S. Cl. ....................... 435/126; 549/315

(58) Field of Classification Search ................ None
See application file for complete search history.

(56) References Cited

U.S. PATENT DOCUMENTS 5,008,193 A * 4/1991 Anderson et al. ........... 435/138
5,817,490 A 10/1998 Hubbs
6,022,719 A * 2/2000 Hubbs ........................ 435/138
6,146,860 A 11/2000 Asakura et al.

OTHER PUBLICATIONS www.chem.qmul.ac.uk/iubmb/enzyme/EC3/2/1/1.html.*
Queen Mary College web site . http://www.googlesyndicatedsearch.com/u/queenmary, Printed Dec. 22, 2007.*
Declerck, N. et al., "Hyperthermostable Mutants of *Bacillus licheniformis* α-Amylase: Multiple Amino Acid Replacements and Molecular Modelling," *Protein Engineering*, vol. 8(10), pp. 1029-1037 (1995).
Yuuki,T. et al., "Complete Nucleotide Sequence of a Gene Coding for Heat- and pH-Stable α-Amylase of *Bacillus licheniformis*: Comparison of the Amino Acid Sequences of Three Bacterial Liquefying α-Amylases Deduced from the DNA Sequences", *Journal of Biochem*, vol. 98(5), pp. 1147-1156 (1985).
Takasaki, Y. et al., "Acid-Stable and Thermostable α-Amylase from *Bacillus licheniformis* α," *Journal of Fermentation and Bioengineering*, vol. 77(1), pp. 94-96 (1994).
Yun, G., et al., "Study on Immobilization of α-amylase from *Bacillus amyloliqusfaciens*," *Biotechnology*, vol. 5(5), pp. 30-32 (1995).
Ying, Z., et al., "Purification and Properties of Thermostable α-Amylase from *Bacillus licheniformis A*. 4041," *Acta Scientiarum Naturalium Universitatis Jilinensis*, vol. 7(3), pp. 85-88 (1997).

* cited by examiner

*Primary Examiner*—David M Naff
*Assistant Examiner*—Kailash C Srivastava
(74) *Attorney, Agent, or Firm*—Bryan Cave LLP

(57) ABSTRACT

A process for producing L-ascorbic acid from 2-keto-L-gulonic acid or D-erythorbic acid from 2-keto-D-gluconic acid by contacting 2-keto-L-gulonic acid or 2-keto-D-gluconic acid, respectively, with an enzym having α-amylase activity in solution. The solvent for this reaction can be water, an aqueous alcohol, an organic solvent or a mixture thereof. In each case, the starting material can be in the form of the free acid, the sodium salt, or the calcium salt.

6 Claims, No Drawings

ENZYMATIC PROCESS FOR THE MANUFACTURE OF L-ASCORBIC ACID AND D-ERYTHORBIC ACID

This application is the National Stage of International Application No. PCT/EP02/12157, filed Oct. 31, 2002.

The present invention relates to a novel process for the manufacture of L-ascorbic acid or D-erythorbic acid from 2-keto-L-gulonic acid or 2-keto-D-gluconic acid, respectively, by using an α-amylase or an enzyme having α-amylase activity.

L-Ascorbic acid, also known as vitamin C, is widely used not only as medicine but also in the field of food industry, cosmetics industry and the like, and is a very useful compound. D-erythorbic acid is mainly used as an antioxidant for food additives.

So far, L-ascorbic acid has been commercially produced by the well-known Reichstein method, in which L-ascorbic acid is produced from D-glucose via D-sorbitol, L-sorbose, diacetone-L-sorbose, diacetone-2-keto-L-gulonic acid, 2-keto-L-gulonic acid, and methyl 2-keto-L-gulonate. In this process, the conversion of D-sorbitol to L-sorbose is the sole microbial step, the others being chemical steps. The conversion of diacetone-2-keto-L-gulonic acid to L-ascorbic acid is achieved by two different procedures: (i) deprotection to give 2-keto-L-gulonic acid, followed by esterification with methanol and base-catalyzed cyclization; and (ii) acid-catalyzed cyclization to L-ascorbic acid directly from the protected or deprotected 2-keto-L-gulonic acid. These conversion processes must be performed by non- or low-water reaction systems. Environmentally and economically, a reaction without organic solvents is preferred.

On the other hand, D-erythorbic acid has been produced from D-glucose via 2-keto-D-gluconic acid, which itself can be produced by fermentation with a strain belonging to the genus *Pseudomonas*, and via methyl 2-keto-D-gluconate.

Much time and effort has been devoted to finding other methods of producing L-ascorbic acid by microorganisms. Most studies on microbial productions of L-ascorbic acid have focused on the production of an intermediate of L-ascorbic acid production, 2-keto-L-gulonic acid, from L-sorbose (e.g. EP 213,591; U.S. Pat. No. 4,960,695; EP 221,707), from D-sorbitol (e.g. EP 213,591; U.S. Pat. No. 5,312,741; WO 95/23220; WO 98/17819], or from D-glucose via 2,5-diketogluconic acid with a single, mixed or recombinant culture. The 2-keto-L-gulonic acid can then be converted into L-ascorbic acid by chemical means as described above.

As mentioned above, the chemical conversion of 2-keto-L-gulonic acid to L-ascorbic acid via 2-keto-L-gulonic acid γ-lactone is an acid-catalyzed reaction accompanying removal of a water molecule. The main principle of the reaction is a carboxyl ester bond formation to make the γ-lactone ring in the 2-keto-L-gulonic acid molecule. Therefore, especially in water phase, the final state in the equilibrium reaction is determined by the physico-chemical conditions. Production of L-ascorbic acid from 2-keto-L-gulonic acid by chemical conversion is considerable even in the water phase, but is not sufficient for commercial application. Production process in water phase or in water phase with low organic solvent content is highly desirable for cost effectiveness and environmental demand. Then, some biological enhancement on the chemical conversion must be desired for the production in water phase. Both high temperature and acidic (low) pH are obviously preferable for the reaction.

WO 97/43433 describes a process for allegedly preparing L-ascorbic acid by contacting 2-keto-L-gulonic acid or an ester thereof with a hydrolase enzyme catalyst selected from the group consisting of proteases (enzyme class EC 3.4.x.x), esterases (enzyme class EC 3.1.x.x), lipases (enzyme class EC 3.1.x.x) and amidases (enzyme class EC 3.5.x.x). Using a hydrolase such as a protease, an esterase, a lipase or an amidase, U.S. Pat. No. 6,022,719 exemplifies the formation of L-ascorbic acid from an ester of 2-keto-L-gulonic acid such as butyl 2-keto-L-gulonate, but no apparent formation of L-ascorbic acid from 2-keto-L-gulonic acid itself. It does not disclose an α-amylase or an enzyme having α-amylase activity as the hydrolase enzyme catalyst for the purpose of L-ascorbic acid formation from 2-keto-L-gulonic acid.

α-Amylase is an endo-type hydrolase which catalyzes hydrolysis of the α-1,4-glucosidic linkages of starch and liberates poly- and oligosaccharide chains of varying lengths. α-Amylases are available from a wide variety of sources, microorganisms, plants, and animals. It has been known that some α-amylases have good thermo-stability. Moreover, the thermoacidophilic bacterium *Alicyclobacillus acidocaldarius* produces an α-amylase, which is highly thermo-stable under acidic condition.

The present invention provides an enzymatic process for the production of L-ascorbic acid from 2-keto-L-gulonic acid, which comprises contacting 2-keto-L-gulonic acid in solution with an α-amylase. Moreover, the present invention also provides an enzymatic process for the production of D-erythorbic acid from 2-keto-D-gluconic acid, which comprises contacting 2-keto-D-gluconic acid in solution with an α-amylase.

As used herein, the term "α-amylase" includes the α-amylase enzyme itself and enzymes having α-amylase activity.

The microorganisms "*Bacillus amyloliquefaciens*", "*Bacillus licheniformis*", and "*Alicyclobacillus acidocaldarius*" also include synonyms or basonyms of such species having the same physico-chemical properties, as defined by the International Code of Nomenclature of Prokaryotes.

The α-amylases used as catalysts in the processes of the present invention are those obtained from organisms including animals, plants, and microorganisms such as fungi, yeast, and bacteria. The preferred α-amylases of the present invention are those of *B. amyloliquefaciens, B. licheniformis, A. acidocaldarius*, and porcine pancreas. More preferred is an enzyme having α-amylase activity of *A. acidocaldarius*, especially *A. acidocaldarius* ATCC 27009.

The α-amylases used in the processes of the present invention may be purchased from suppliers such as Sigma-Aldrich Co. (St. Louis, USA) or may be isolated from any appropriate organisms including animals, plants, and microorganisms by usual protein purification methods such as ammonium sulfate precipitation, chromatography, and crystallization. In the processes of the present invention, any form of α-amylase can be used, in particular an enzyme solution or the immobilized enzyme.

In the processes of the present invention, the preferred chemical form of 2-keto-L-gulonic acid and 2-keto-D-gluconic acid are the free acids or their metal salts such as sodium and calcium salts.

The reaction mixture may contain a suitable stabilizer for α-amylase such as a Ca ion and may further contain an antioxidant such as 2-mercaptoethanol, dithiothreitol, or cysteine to prevent the degradation of the produced L-ascorbic acid or D-erythorbic acid.

The reaction temperatures for the process of the present invention are in the range of from 0° C. to 120° C. The preferred temperatures are in the range of from 20° C. to 100° C., and most preferably in the range of from 37° C. to 90° C.

Suitable pHs for the processes of the present invention are in the range of from 1.5 to 12. The preferred pHs are in the range of from 1.5 to 8, and most preferably in the range of from 2 to 7. The pH of the reaction mixture may be adjusted by using suitable buffers or may be directly adjusted by addition of acid e.g., HCl or alkali e.g., NaOH.

The reaction period is suitably in the range of from 1 to 7 days, preferably in the range of from 1 to 3 days.

The process of the present invention may be performed in a solvent such as water, an aqueous alcohol, an organic solvent or a mixture thereof. Examples of an alcohol include a $C_1$-$C_6$alcohol, such as methanol, ethanol, n-propanol, iso-propanol, n-butanol, iso-butanol, or tert.-butanol. Examples for organic solvents include aliphatic hydrocarbons (e.g., heptane and iso-octane), alicyclic hydrocarbon (e.g., cyclohexane), and aromatic hydrocarbons (e.g., benzene and toluene). The preferred solvent is water or an aqueous solvent.

The L-ascorbic acid or D-erythorbic acid produced under the conditions as described above can easily be recovered by methods known in the art. For example, the L-ascorbic acid or D-erythorbic acid can be isolated by crystallization, electrodialysis, or column chromatography by using ion exchange resin.

The present invention is explained in more detail by referring to the following Examples; however, it should be understood that the present invention is not limited to those particular Examples.

EXAMPLE 1

Conversion of 2-keto-L-gulonic acid to L-ascorbic acid by α-amylases of *B. amyloliquefaciens*, *B. licheniformis*, and Porcine Pancreas The α-amylases of *B. amyloliquefaciens* (Sigma-Aldrich, product number 10068), *B. licheniformis* (Sigma-Aldrich, product number A4551), and porcine pancreas (Sigma-Aldrich, product number A4268) were tested for the conversion of 2-keto-L-gulonic acid to L-ascorbic acid. The enzyme powders were dissolved in buffer 1 [20 mM Na-MES buffer (pH 7.0) and 2 mM $CaCl_2$] and used for the conversion reaction. The reaction mixture contained 12% sodium 2-keto-L-gulonic acid monohydrate, 2 mM $CaCl_2$, and the α-amylase in 50 µl of 100 mM buffer. The concentration of the α-amylase and the buffer in each reaction mixture is shown in Table 1. The reaction was carried out under anaerobic condition at 70° C. for 20 hours.

L-Ascorbic acid was assayed by HPLC on YMC-Pack PolyamineII column (ID. 4.6×150 mm; YMC Co., Japan) at 264 nm with the mobile-phase solvent containing 70% (v/v) acetonitrile and 15 mM ammonium dihydrogenphosphate at a flow rate of 1.5 ml/min. Amounts of biologically produced L-ascorbic acid were determined by the difference between results from the reactions with and without the α-amylase. The amounts of L-ascorbic acid produced are summarized in Table 1.

TABLE 1

| α-Amylase* | Enzyme (µg/ml) | Buffer (pH) | L-Ascorbic acid (mg/l) |
|---|---|---|---|
| 10068 | 400 | Na-MES (pH 6.0) | 29.1 |
| A4551 | 320 | Na-acetate (pH 5.0) | 84.9 |
| A4268 | 400 | Na-MES (pH 5.5) | 61.9 |

*product number

EXAMPLE 2

Purification of an Enzyme Having α-amylase Activity from *A. acidocaldarius*

*A. acidocaldarius* ATCC 27009 was aerobically grown in 24.6 l of a medium consisting of 9.8 mM $(NH_4)_2SO_4$, 0.47 mM $CaCl_2$, 2.7 mM $KH_2PO_4$, 1.0 mM $MgSO_4$, 10 µM $FeSO_4$, 9.1 µM $MnCl_2$, 11.7 µM $Na_2B_4O_7$, 0.57 µM $ZnSO_4$, 0.2 µM $CuCl_2$, 0.12 µM $VOSO_4$, 0.16 µM $NaMoO_4$, 30 nM $CoSO_4$, and 10 mM maltose (pH 3.5) at 55° C. for 15 hours. The culture fluid was recovered by centrifugation.

During the enzyme purification, all runs of column chromatography were carried out at 4° C. The α-amylase activity was determined by the spectrophotometric assay by using p-nitrophenyl α-D-maltopentoside (Sigma-Aldrich) as a substrate. The assay mixture contained 1 mM p-nitrophenyl α-D-maltopentoside and an enzyme sample in 40 µl of 50 mM Na-acetate buffer (pH 4.0). After incubating at 55° C. for 20 minutes, 100 µL of 1 M Tris-HCl buffer (pH 7.5) was added to the reaction mixture. The released p-nitrophenol was detected as an absorbance at 405 nm.

The recovered culture fluid was subjected to DEAE Sepharose Fast Flow (Amersham Pharmacia Biotech UK Ltd. Buckinghamshire, UK) column chromatography. 0.5 M Na-MES buffer (pH 6.0) was added to the culture fluid at 20 mM and the pH was adjusted to 6.0 with NaOH. The prepared fluid sample from 1.65 l culture was loaded on DEAE Sepharose Fast Flow column (100 ml: I.D. 4.4×6.6 cm) equilibrated with buffer 2 [20 mM Na-MES buffer (pH 6.0), 0.5 mM $CaCl_2$, and 1.0 mM $MgSO_4$]. After washing with buffer 2, the enzyme was eluted with a linear gradient of NaCl (0-0.45 M in buffer 2). This step was repeated four times to treat 6.6 l of culture. The active fractions of four chromatography runs were brought together and dialyzed against buffer 3 [20 mM Na-acetate buffer (pH 3.0), 0.5 mM $CaCl_2$, and 1.0 mM $MgSO_4$]. The dialyzed sample was loaded on SP Sepharose Fast Flow column (80 ml: I.D. 4.4×5.3 cm, Amersham Pharmacia Biotech UK) equilibrated with buffer 3. After washing with buffer 3, the enzyme was eluted with a linear gradient of NaCl (0-0.6 M in buffer 3). The active fractions were collected. After dialysis against buffer 2, the enzyme sample was loaded on Q Sepharose Fast Flow column (30 ml: I.D. 2.5×6.2 cm, Amersham Pharmacia Biotech UK) equilibrated with buffer 2. After washing with buffer 2, the enzyme was eluted with a linear gradient of NaCl (0-0.8 M in buffer 2). The active fractions were collected and concentrated to 3.5 ml with Centriplus YM-30 (Millipore Co., USA). The concentrated sample was passed through HiPrep Seph-acryl S-300 HR 16/60 (Amersham Pharmacia Biotech UK) with buffer 4 [20 mM Na-MES buffer (pH 6.0), 0.5 mM $CaCl_2$, 1.0 mM $MgSO_4$, and 0.15 M NaCl]. A fraction of 9 ml containing the enzyme having α-amylase activity was obtained. The enzyme sample was dialyzed against buffer 5 [20 mM Na-MES buffer (pH 6.0), 0.5 mM $CaCl_2$, 1.0 mM $MgSO_4$, and 50 mM NaCl] and concentrated to 0.11 ml by repeated concentration/dilution in a concentrator with Centricon YM-30 (Millipore Co., USA). On SDS-PAGE, the purified enzyme mainly exhibited a molecular mass of approximately 160 kDa. Finally, 0.47 mg of the enzyme having α-amylase activity with the purity of about 80% was obtained.

EXAMPLE 3

Conversion of 2-keto-L-gulonic Acid to L-ascorbic Acid by an Enzyme Having α-amylase Activity of *A. acidocaldarius*

The enzyme having α-amylase activity purified from *A. acidocaldarius* in Example 2 was tested for the conversion of 2-keto-L-gulonic acid to L-ascorbic acid. The reaction mixture contained 10% sodium 2-keto-L-gulonic acid monohydrate (adjusted to pH 2.5 with HCl) and the enzyme (100 or 200 μg/ml) in 20 μl. The reaction was carried out under anaerobic conditions at 80° C. for 24 hours. L-ascorbic acid was assayed by the method described in Example 1. Amounts of biologically produced L-ascorbic acid were determined by the difference between results from the reactions with and without the enzyme. 100 μg/ml enzyme produced 3.90 g/l L-ascorbic acid, 200 μg/ml enzyme produced 4.22 g/l L-ascorbic acid.

EXAMPLE 4

Conversion of 2-keto-D-gluconic Acid to D-erythorbic Acid by α-amylases of *B. amyloliquefaciens, B. licheniformis*, and Porcine Pancreas The α-amylases of *B. amyloliquefaciens, B. licheniformis*, and porcine pancreas described in Example 1 were tested for the conversion of 2-keto-D-gluconic acid to D-erythorbic acid. The α-amylases dissolved in buffer 1 were used for the conversion reaction. The reaction mixture contained 5% 2-keto-D-gluconic acid hemicalcium salt (Sigma-Aldrich), 4 mM $CaCl_2$, and 400 μg/ml of the α-amylase per ml in 50 μl of 100 mM buffer. The buffer in each reaction mixture is shown in Table 3. The reaction was carried out under anaerobic conditions at 70° C. for 20 hours. D-Erythorbic acid was assayed by the same method as for L-ascorbic acid (described in Example 1). Amounts of biologically produced D-erythorbic acid were determined by the difference between results from the reactions with and without the α-amylase. The amounts of D-erythorbic acid produced are summarized in Table 2.

TABLE 2

| α-Amylase* | Enzyme (μg/ml) | Buffer (pH) | D-Erythorbic acid (mg/l) |
|---|---|---|---|
| 10068 | 400 | Na-acetate (pH 5.0) | 64.7 |
| A4551 | 400 | Na-acetate (pH 5.0) | 69.5 |
| A4268 | 400 | Na-MES (pH 5.5) | 60.5 |

*product number

EXAMPLE 5

Conversion of 2-keto-D-gluconic Acid to D-erythorbic Acid by Enzymes Having α-amylase Activity of *A. acidocaldarius*

The enzyme purified from *A. acidocaldarius* in Example 2 was tested for the conversion of 2-keto-D-gluconic acid to D-erythorbic acid. The reaction mixture contained 5% 2-keto-D-gluconic acid hemicalcium salt (adjusted to pH 2.5 with HCl) and the enzyme (0 or 200 μg/ml) in 20 μl. The reaction was carried out under anaerobic conditions at 70° C. for 21 hours. D-Erythorbic acid was assayed by the method described in Example 4. The amount of biologically produced D-erythorbic acid was determined by the difference between results from the reactions with and without the enzyme. 76.0 mg/l of D-erythorbic acid was produced by the reaction with the enzyme.

The invention claimed is:

1. A process for preparing L-ascorbic acid from 2-keto-L-gulonic acid or preparing D-erythorbic acid from 2-keto-D-gluconic acid which comprises contacting a solution comprising 2-keto-L-gulonic acid or its metal salt or 2-keto-D-gluconic acid or its metal salt, respectively, with an enzyme which is an α-amylase or an endo-type hydrolase at a pH in the range of from 2 to 7, wherein the enzyme catalyzes the hydrolysis of the α-1,4-glucosidic linkage of starch to form L-ascorbic acid or D-erythorbic acid.

2. The process according to claim 1, wherein the solution further comprises a solvent which is selected from the group consisting of water, an aqueous alcohol, an organic solvent, and a mixture thereof.

3. The process according to claim 1, wherein 2-keto-L-gulonic acid, or 2-keto-D-gluconic acid is contacted with the enzyme at a temperature in the range of from 20° C. to 120° C.

4. The process according to claim 1, wherein the metal salt of 2-keto-L-gulonic acid or the metal salt of 2-keto-D-gluconic acid is a sodium salt or a calcium salt.

5. The process according to claim 3, wherein 2-keto-L-gulonic acid, or 2-keto-D-gluconic acid is contacted with the enzyme at a temperature in the range of 20° C. to 100° C.

6. The process according to claim 5, wherein 2-keto-L-gulonic acid, or 2-keto-D-gluconic acid is contacted with the enzyme at a temperature in the range of 37° C. to 90° C.

* * * * *